United States Patent [19]
Ellis

[11] Patent Number: 4,648,391
[45] Date of Patent: Mar. 10, 1987

[54] STABILIZER FOR PERCUTANEOUS MEDICAL DEVICES

[75] Inventor: Willard H. Ellis, Round Rock, Tex.

[73] Assignee: Carbomedics, Inc., Austin, Tex.

[21] Appl. No.: 798,936

[22] Filed: Nov. 18, 1985

[51] Int. Cl.⁴ .............................................. A61F 15/00
[52] U.S. Cl. ............................... 128/132 R; 604/175; 604/180
[58] Field of Search .................. 128/132 R, 133, 149, 128/153, 154; 604/175, 180

[56] References Cited

U.S. PATENT DOCUMENTS

| | | | |
|---|---|---|---|
| 2,367,690 | 1/1945 | Purdy | 128/132 R |
| 3,528,416 | 9/1970 | Chamberlain | 128/154 |
| 4,491,126 | 1/1985 | Cullor | 604/175 X |
| 4,559,039 | 12/1985 | Ash et al. | 604/175 |

Primary Examiner—Dalton L. Truluck
Attorney, Agent, or Firm—Fulbright & Jaworski

[57] ABSTRACT

A protective stabilizer cap for use with a percutaneous device. The cap includes an annulate band carrying an ahesive for cutaneous contact in juxtaposition with the percutaneous device so that relative motion is between the percutaneous device and the skin is restricted.

13 Claims, 4 Drawing Figures

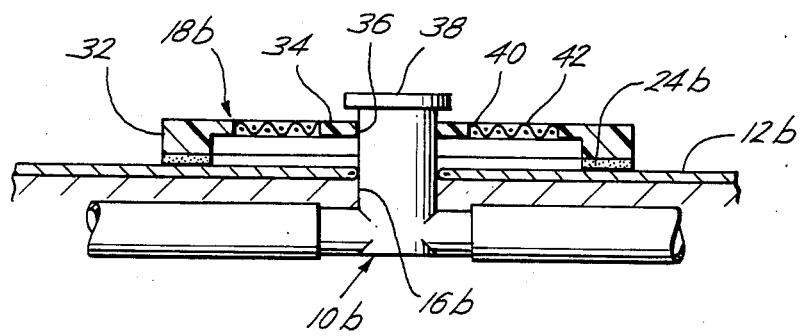
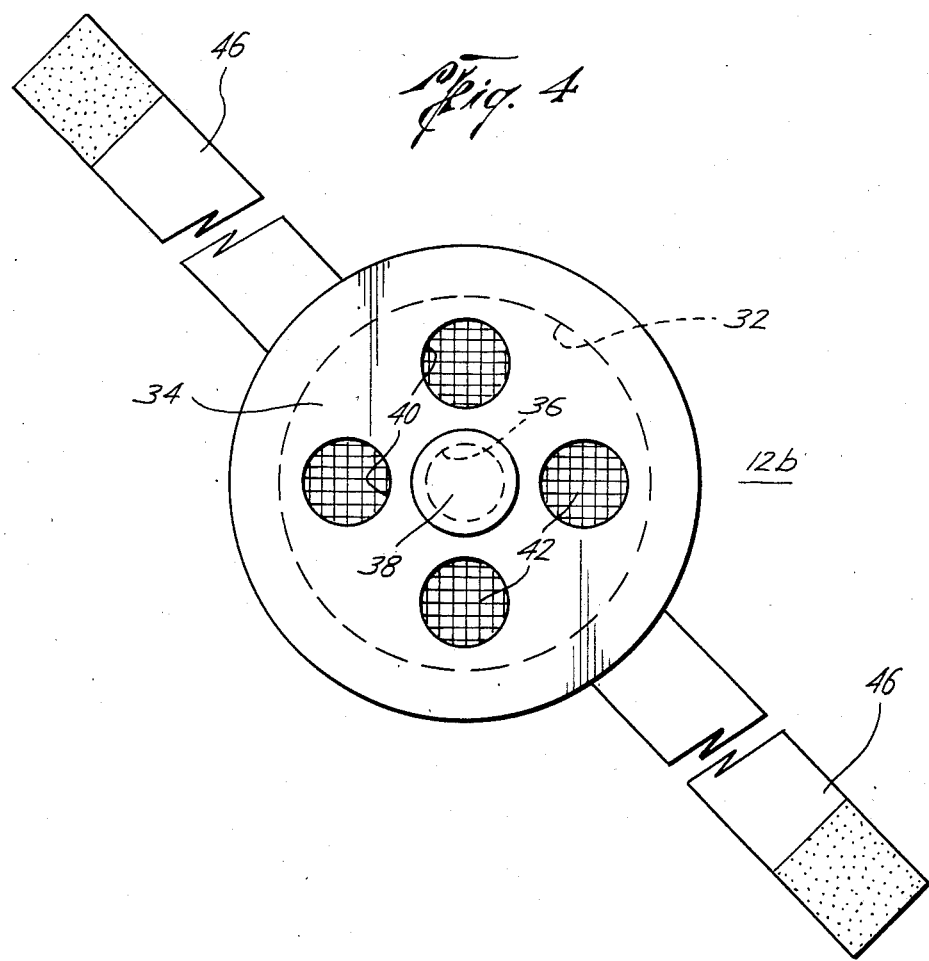

STABILIZER FOR PERCUTANEOUS MEDICAL DEVICES

BACKGROUND OF THE INVENTION

Various percutaneous devices are implanted for long-term or permanent access through the skin. A typical percutaneous device is a blood-access device that may be opened and closed repetitively for dialysis purposes. Other percutaneous medical devices include infusion pumps, conduits for long-term delivery of drugs, devices for nerve stimulation, etc. In the use of these devices, it is important that movement of the skin relative to such devices be eliminated or restricted so as to reduce cutaneous trauma. Indeed, in many instances, it is important that the skin immediately adjacent to the percutaneous device heal and remain healthy to minimize the possibility of bacterial infection. At the same time, it is important that the skin around these devices have access to air.

Unfortunately, permanently implanted percutaneous devices commonly develop exit site infections which often necessitates removal of a functioning device. Relative motion between the device-tissue interface inhibits tissue attachment to the device, and the resulting poor seal allows infectious organisms to penetrate into the seal interface. Various approaches have been proposed to prevent the trauma noted above such as reinforcing the skin tissue around the opening so that the stress is concentrated elsewhere and the interface between the percutaneous device and the skin is protected. However, reinforcement typically connotes surgical procedures which can be tedious and without assurances of success.

SUMMARY OF THE INVENTION

The present invention is directed to a protective stabilizer cap for use with a percutaneous device, the stabilizer cap having a cap means which may be an annulate member with a surface adapted peripherally for cutaneous contact in juxtaposition with the percutaneous device. An adhesive means is provided for removably affixing the cap means to skin about the percutaneous device so that relative motion as between the percutaneous device and the skin is restricted. The cap means preferably is constructed so as to permit passage of air through but restrict penetration of infectious organisms.

A method is provided whereby a first such cap is applied as described and later is replaced with a second cap having an annulate band of a diameter different from the diameter of the annulate band of the first cap for adhesion to a substantially different skin area. Thus, alternating skin areas are used successively in order that no single area of skin is subjected to prolonged deprivation of air. This procedure is simple, relatively inexpensive and dispenses with the more cumbersome surgical reinforcement of tissue around the opening for the percutaneous device.

Thus, an object of the present invention is the provision of a protective stabilizer cap for use with a percutaneous device and a method for stabilizing a percutaneous device against relative motion with respect to the cutaneous surface penetrated by said device.

Another object of the present invention is the provision of such a protective stabilizer cap having an annulate band with a surface for cutaneous contact surrounding but spaced apart from the percutaneous device, such surface carrying an adhesive means for removably affixing the cap to skin.

Still another object of the present invention is the provision of a protective stabilizer cap formed and adapted so as to be in engagement with the percutaneous device to further reduce relative motion between the percutaneous device and the skin.

Still a further object of the present invention is the provision of a cap with a cover means formed of sufficiently transparent material as to permit viewing of skin conditions thereunder while in place.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 3 is an elevation view, partly in cross section, illustrating yet another embodiment of the stabilizer cap of the present invention wherein the cap is provided with filter openings for passage of air therethrough.

FIG. 4 is a plan view of the embodiment shown in FIG. 3.

DESCRIPTION OF THE PREFERRED EMBODIMENT

Figure 1:
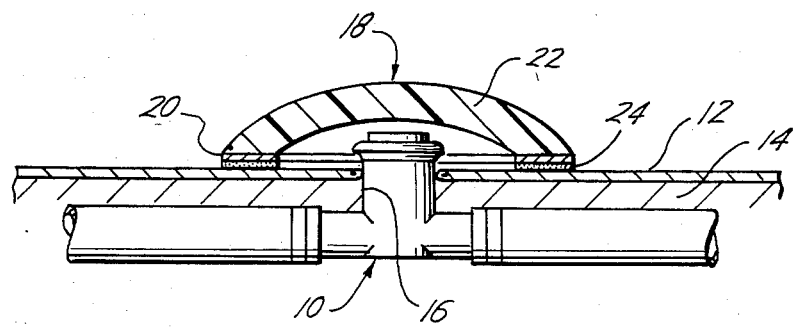
FIG. 1 is an elevation view, partly in cross section, of a protective stabilizer cap shown in relation to a percutaneous device.

Permanently implanted percutaneous devices commonly develop exit site infections which often necessitates removal of a functioning device. Relative motion between the device and skin at the device-tissue interface inhibits tissue attachment to the device, and the resulting poor seal allows infectious organisms to penetrate into the seal interface. An example of a percutaneous device of this sort is a blood access device 10 illustrated in FIG. 1. For purposes of this application, blood access devices and percutaneous devices are conventional and form no part of the invention as such. These devices typically are implanted subcutaneously as illustrated in FIG. 1, the reference character 12 indicating skin or cutaneous layers and the reference character 14 indicating subcutaneous layers of body tissue. It is important that the skin tissue 12 immediately adjacent the penetrating portion 16 of the percutaneous device 10 be attached firmly to the device and, once attached, remain so. Any relative movement as between the skin 12 and the percutaneous device 10 naturally tends to dislodge the skin from about the penetrating or extended portion 16 of the blood access device resulting in a poor seal.

The stabilizer cap of the present invention restricts the relative motion described above through the provision of cap means 18 having a surface adapted peripherally for cutaneous contact in juxtaposition with the percutaneous device. The cap means 18 includes an annulate band 20 having a surface for cutaneous contact, that is, contact with the skin 12, surrounding but spaced apart from the extended portion 16 of the percutaneous device. Either attached to or formed integrally of the annulate band 20 is a cover 22 shown in FIG. 1 in a dome configuration so as to enclose the skin area around the percutaneous device. The stabilizer cap 18 is removably affixed to the skin 12 by use of adhesive shown in FIG. 1 as the layer 24. Any suitable adhesive may be used so long as it permits the stabilizer cap 18 to be firmly affixed to the skin 12 and yet is removable without undue irritation to the skin 12 and without jeopardizing tissue attachment to the percutaneous device. An example of a suitable adhesive that may be employed for this purpose is sold under the trademark Stomahesive by Convatech, P.O. Box 4000, Princeton, N.J. 08540.

While the annulate band 20 and cover 22 are circular in the embodiment illustrated in FIG. 1, it will be understood that the annulate band may have any other suitable curvilinear or even a multi-sided geometric configuration. Also, the cover 22 may have a configuration other than the dome shape illustrated in FIG. 1. Similarly, the dimensions of the band and cover may vary but should remain within limits such that, upon adhesion of the cap to the skin, relative motion as between the percutaneous device and the skin is restricted.

Figure 2:
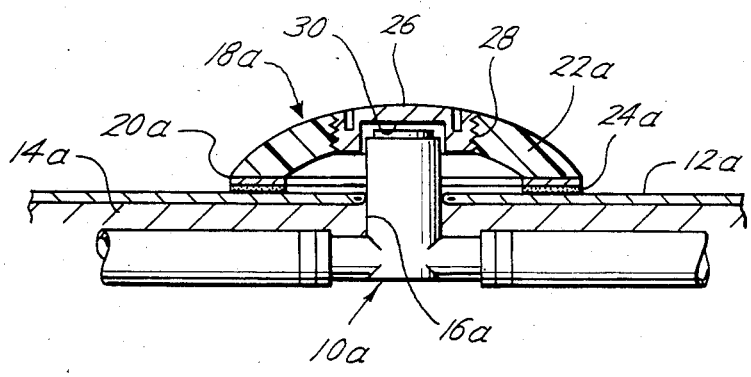
FIG. 2 is an elevation view, partly in cross section, illustrating a modification of the stabilizer cap for engageable contact with a percutaneous device.

The embodiment illustrated in FIG. 2 is similar to that of FIG. 1 except that the stabilizer cap is adapted to be in substantial contact with the percutaneous device. Preferably, as shown in the drawing, the cover 22a of the stabilizer cap 18a is provided with a center access portion 26 having threads 28 that threadably engage similar threads formed in the cover 22a. Thus, the access cap 26 may be opened so as to carry out the necessary functions vis-a-vis the percutaneous device 10a without removing the remaining portion of the stabilizer cap 18a. This feature reduces further any risk of damage to the interface of the skin tissue and the percutaneous device.

Again with respect to the embodiment of FIG. 2, the access cap portion 26 of the cover 22a carries a recess portion 30 which provides a space for and receives the extended portion 16a of the percutaneous device 10a. The recess 30 should be formed slightly larger than the outer extremity of the extension 16a of the percutaneous device, permitting engageable contact of the percutaneous device with the stabilizer cap. As a result, any movement of the stabilizer cap 18a and the skin 12a to which it is attached causes the percutaneous device 10a to move as a unit to promote an even more stable interface between the skin tissue and the percutaneous device. It will be appreciated that the recess 30 may be provided in the embodiment of FIG. 1 and is not dependent on the use or not of the access cover portion 26.

Referring now to FIGS. 3 and 4, yet a further embodiment of the stabilizer cap of the present invention is illustrated wherein the annulate band 32 is integrally formed with the cover 34 in a flattened, disk configuration. The annulate band 32, as in prior embodiments, is provided with adhesive material 24b to permit removable attachment to the skin surface 12b. The cover 34 is provided with a central opening 36 to receive the extended portion 16b of the percutaneous device 10b. In this embodiment, the percutaneous device 10b is shown having a cap member 38. In this configuration, the opening 36 of the cover 34 provides engageable contact between the stabilizer cap and the extended portion of the percutaneous device which again permits the skin 12b and stabilizer cap 18b to move as a unit with the percutaneous device 10b.

The embodiment illlustrated in FIGS. 3 and 4 provides the additional feature of permitting passage of air through the stabilizer 18b but restricting penetration of infectious organisms. This is accomplished through the provision of a plurality of holes 40 formed in the cover 34, the holes 40 being sealed with filters made from a suitable cloth or paper-like material 42 that permits movement of air therethrough but resists penetration of infectious organisms and other foreign bodies. Examples of suitable filter materials that may be employed for this purpose are sold under the trademarks Hydrophob and Durapore by Millipore, South San Francisco, Calif. Thus, the cutaneous area 12b has access to air so as to permit a healthy skin condition and tissue interface with the percutaneous device.

FIG. 4 illustrates the optional feature of a band 46 suitably secured to the stabilizer 18b. The band may extend about a body extremity such as an arm to further secure the stabilizer in position. Velcro type materials may be used for puposes of joining the ends of the band.

Preferably, the stabilizer cap of the present invention is a disposable item in the sense that it may be discarded after a period of use and replaced by a similar device. A distinct advantage of the present invention is that, upon replacement of a stabilizer cap, the replacement unit may have an annulate band of a diameter different from the diameter of the preceding annulate band for adhesion to a substantially different skin area. This allows the skin previously in contact with the adhesive of the annulate band to regenerate to a healthy state, and successive use of stabilizer caps of differing diameters promotes overall good health of the skin area around the percutaneous device.

The annulate band and cover of the stabilizer cap of the present invention may be formed either separately or integrally of materials such as Polysulfone (trademark for a resin manufactured and marketed by Union Carbide Corporation), polycarbonate and other such durable materials. The width of the annulate band for purposes of receiving the adhesive material will vary depending upon circumstances of use. A width of ⅛th inch has been found acceptable. The overall diameter of the stabilizer cap (determined by the outside diameter of the annulate band) likewise may vary, but approximately 1⅜th inch has been found suitable. Variations of such diameter may be made to promote skin health as previously explained. Finally, the overall height of the stabilizer cap (i.e., the distance from the higest point of the outside surface of the cover to the lower surface of the annulate band which carries the adhesive material) may vary, approximately ⅜th inch being suitable. Of course, the height dimension will vary among embodiments illustrated in the drawings depending upon engagement or not of the stabilizer cap with the percutaneous device.

It may be desirable in some instances to form the stabilizer cap or at least the cover portion thereof of a sufficiently transparent material as to permit viewing of skin conditions thereunder. This will permit frequent inspection of not only the skin condition but also the interface of skin tissue with the percutaneous device.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts may be made without departing from the spirit of the invention and the scope of the appended claims.

What is claimed is:

1. A protective stabilizer cap for use with a percutaneous device comprising, (a) substantially inflexible cap means having a surface adapted peripherally for cutaneous contact in juxtaposition with the percutaneous device, and (b) adhesive means for removably affixing the cap means (a) to skin about the percutaneous device so that relative motion as between the percutaneous device and the skin is restricted.

2. The stabilizer cap of claim 1 wherein, more specifically, the cap means (a), includes, (i) a substantially inflexible annulate band having a surface for cutaneous contact surrounding but spaced apart from the percutaneous device, said surface carrying the adhesive means (b), (ii) cover means attached to and enclosing the band (i), permitting passage of air therethrough but restricting penetration of infectious organisms.

3. The stabilizer cap of claim 1 wherein, more specifically, the substantially inflexible cap means (a) includes means for providing substantial contact with the percutaneous device.

4. The stabilizer cap of claim 1 wherein, more specifically, the substantially inflexible cap means (a) includes means for providing engagement with the percutaneous device to reduce relative motion between the percutaneous device and the skin.

5. The stabilizer cap of claim 2 wherein, more specifically, the annulate band (i) is of a curvilinear or multi-sided configuration.

6. The stabilizer cap of claim 2 wherein the cover means (ii) is formed of sufficiently transparent material as to permit viewing of skin conditions thereunder.

7. The stabilizer cap of claim 1 wherein the adhesive means (b) comprises an adhesive material suitable for contact with skin.

8. A protective stabilizer cap for use with a percutaneous device, comprising, (a) a cap formed of a substantially inflexible material with (i) a generally circular band having a surface for cutaneous contact surrounding but spaced apart from the percutaneous device, and (ii) a cover affixed to the band, and (b) adhesive means for removably affixing the cap means (a) to skin about the percutaneous device so that relative motion as between the percutaneous device and the skin is reduced.

9. The stabilizer cap of claim 8 wherein the adhesive means (b) comprises an adhesive material suitable for contact with skin.

10. The stabilizer of claim 8 wherein, more specifically, the cap (a) includes means for engagement with the percutaneous device to reduce relative motion between the percutaneous device and the skin.

11. The protective stabilizer cap of claim 8 wherein the cover (a)(ii) permits passage of air therethrough but restricts penetration of infectious organisms.

12. A method for stabilizing a percutaneous device against relative motion with the cutaneous surface penetrated by said device, comprising the steps of, (a) removably adhering a first cap having an annulate band to skin surrounding the percutaneous device, said annulate band providing a surface for adhesion of the cap to the skin in spaced relation with the percutaneous device, and (b) replacing said first cap with a second cap having an annulate band of a diameter different from the diameter of the annulate band of the first cap for adhesion to a substantially different skin area.

13. The method of claim 12 wherein either or both the first and second caps are in engagement with the percutaneous device.

* * * * *